US008056399B2

(12) United States Patent
Thompson et al.

(10) Patent No.: US 8,056,399 B2
(45) Date of Patent: Nov. 15, 2011

(54) LIQUID GAS VAPORIZATION AND MEASUREMENT SYSTEM AND METHOD

(75) Inventors: Kenneth O. Thompson, Ravenswood, WV (US); Walter F. Grehold, Sherman, WV (US)

(73) Assignee: Mustang Sampling, LLC, Murraysville, WV (US)

( * ) Notice: Subject to any disclaimer, the term of this patent is extended or adjusted under 35 U.S.C. 154(b) by 467 days.

(21) Appl. No.: 12/364,208

(22) Filed: Feb. 2, 2009

(65) Prior Publication Data

US 2009/0151427 A1 Jun. 18, 2009

Related U.S. Application Data

(63) Continuation-in-part of application No. 11/358,724, filed on Feb. 22, 2006, now Pat. No. 7,484,404.

(60) Provisional application No. 60/654,472, filed on Feb. 22, 2005.

(51) Int. Cl.
*G01N 1/00* (2006.01)
(52) U.S. Cl. ...................................... 73/61.59
(58) Field of Classification Search .................. 73/61.59
See application file for complete search history.

(56) References Cited

U.S. PATENT DOCUMENTS

| | | | |
|---|---|---|---|
| 2,665,239 A | | 1/1954 | Howard et al. |
| 3,609,983 A | * | 10/1971 | Lofredo et al. ................. 62/648 |
| 3,661,202 A | * | 5/1972 | Moore, Jr. ................. 165/104.26 |
| 3,933,030 A | | 1/1976 | Forster et al. |
| 5,505,782 A | * | 4/1996 | Stauffer ........................ 118/726 |
| 5,918,595 A | * | 7/1999 | Olsson et al. ............ 128/203.26 |
| 6,408,895 B1 | * | 6/2002 | Beam .............................. 141/59 |
| 6,827,046 B2 | | 12/2004 | Welle |
| 6,848,502 B2 | | 2/2005 | Bishop et al. |
| 7,337,616 B2 | | 3/2008 | Meneses et al. |

OTHER PUBLICATIONS

Foss, Michelle M. Ph.D., "Introduction to LNG; An Overview on liquefied natural gas (LNG), its properties, the LNG industry, safety considerations", Energy Economics Research at the Bureau of Economic Geology, Center for Energy Economics, Jan. 2003.
Tarlowski, Janusz, et al., "LNG Import Terminals—Recent Developments," 2005.
United States of America Federal Energy Regulatory Commission, "Notice of Availability of Staff's Responses to Comments on the Consequence Assessment Methods for Incidents Involving Releases from Liquefied Natural Gas Carriers," Jun. 18, 2004.
Energy Information Administration, "U.S. Natural Gas Markets: Mid Term Prospects for Natural Gas Supply", Dec. 2001.
Energy Information Administration, Office of Oil and Gas, "U.S. LNG Markets and Uses," Jan. 2003.

* cited by examiner

*Primary Examiner* — Hezron E Williams
*Assistant Examiner* — Alex Devito
(74) *Attorney, Agent, or Firm* — Cahn & Samuels, LLP (57) ABSTRACT

A liquid gas vaporization and measurement system, and associated method, for efficiently vaporizing a continuous sample of liquid gas, such as liquid natural gas (LNG), and accurately determining the constituent components of the gas. A constant flow of liquid gas sampled from a mass storage device is maintained in a vaporizing device. Within the vaporizing device the liquid gas is flash vaporized within heated narrow tubing. The liquid gas is converted to vapor very quickly as it enters one or more independently operating vaporizer stages within the vaporizing device. The vapor gas is provided to a measuring instrument such as a chromatograph and the individual constituent components and the BTU value of the gas are determined to an accuracy of within +/−0.5 mole percent and 1 BTU, respectively.

38 Claims, 10 Drawing Sheets

LIQUID GAS VAPORIZATION AND MEASUREMENT SYSTEM AND METHOD

I. CROSS REFERENCE TO RELATED APPLICATIONS

This application is a continuation-in-part application of U.S. Ser. No. 11/358,724 filed on Feb. 22, 2006, now U.S. Pat. No. 7,484,404, and claims priority of Provisional Application Ser. No. 60/654,472, filed on Feb. 22, 2005, the entire contents of both the patent and the provisional application are incorporated herein by reference.

II. FIELD OF THE INVENTION

This invention relates generally to a system and method for the efficient vaporization and measurement of liquid natural gas (LNG). More particularly, the invention relates to a system and method for continuously and efficiently vaporizing an LNG shipment, or portion thereof, into its gaseous form in order to accurately determine the constituent components and British Thermal Unit (BTU) value of the LNG shipment.

III. BACKGROUND OF THE INVENTION

Natural gas is a combustible, gaseous mixture of several different hydrocarbon compounds and is typically extracted from deep underground reservoirs formed by porous rock. The composition of natural gas extracted from different reservoirs varies depending on the geographic location of the reservoir. In fact, it is not entirely uncommon for the composition of gas extracted from a single given reservoir to vary to an extent. Regardless of any variations, however, the primary component of natural gas is methane, a colorless, odorless, gaseous saturated hydrocarbon. Methane usually accounts for 80% to 95% of any natural gas sample and the balance is composed of varying amounts of ethane, propane, butane, pentane and other hydrocarbon compounds.

Natural gas is used extensively in residential, commercial and industrial applications. It is the dominant energy used for home heating with well over half of American homes using natural gas. The use of natural gas is also rapidly increasing in electric power generation and cooling, and as a transportation fuel.

Natural gas, like other forms of heat energy, is measured in British thermal units or Btu. One Btu is equivalent to the heat needed to raise the temperature of one pound of water by one degree Fahrenheit at atmospheric pressure.

A cubic foot of natural gas has about 1,027 BTU. Natural gas is normally sold from the wellhead, i.e., the point at which the gas is extracted from the earth, to purchasers in standard volume measurements of thousands of cubic feet (Mcf). However, consumer bills are usually measured in heat content or therms. One therm is a unit of heating equal to 100,000 BTU.

Three separate and often independent segments of the natural gas industry are involved in delivering natural gas from the wellhead to the consumer. Production companies explore, drill and extract natural gas from the ground; transmission companies operate the pipelines that connect the gas fields to major consuming areas; and distribution companies are the local utilities that deliver natural gas to the customer.

In the United States alone, natural gas is delivered to close to 200 million consumers through a network of underground pipes that extends over a million miles. To produce and deliver this natural gas there are over a quarter-million producing natural gas wells, over one hundred natural gas pipeline companies and more than a thousand local distribution companies (LDCs) that provide gas service to all 50 states.

Prior to regulatory reform, which essentially restructured the industry, producers sold gas to the pipeline companies, who sold it to the LDCs, who sold it to residential and other customers. Post-regulation, however, pipeline companies no longer purchase gas for resale. Instead, the pipeline companies merely transport gas from sellers, such as producers or marketers, to buyers, such as electric utilities, factories and LDCs. Thus, the LDCs now can choose among a variety of sellers of natural gas, whereas before they could only buy gas from one source, i.e., the pipeline company. Further, some states have implemented additional restructuring which renders the LDCs subject to regulation by State public utility commissions. Prior to these additional state regulations, an LDC's residential customers could only buy gas from one source, i.e., the LDC. After state regulation, however, residential customers can choose a different supplier other than their LDC from which to buy the gas. The consumer's LDC, as the owner/operator of the distribution network, delivers the gas to the consumer, as before, but the LDC only charges the consumer for delivery of the gas and the independent supplier bills for the gas.

Thus, natural gas is very important to the U.S. energy supply. Consumption of natural gas in the United States, however, has increased beyond the available supply of domestic natural gas. One available option to increase supply is to increase imports of liquefied natural gas (LNG).

More particularly, according to one estimate natural gas consumption in the United States is expected to increase from about 22 trillion cubic feet (Tcf) in 2004 to almost 31 Tcf by 2025. Accordingly, domestic production combined with imports via pipeline from Canada will be insufficient to meet the demand. In response, a small but growing percentage of gas supplies are imported and received as LNG via tanker ships.

LNG is produced by taking natural gas from a production field, removing impurities, and liquefying the natural gas. In the liquefaction process, the gas is cooled to a temperature of approximately −260 degrees F. One volume of this condensed liquid form of natural gas occupies about $\frac{1}{600}$th of the volume of natural gas at a stove burner tip. The LNG is loaded onto double-hulled ships which are used for both safety and insulating purposes. Once the ship arrives at the receiving port, the LNG is typically off-loaded into well-insulated storage tanks. Vaporization or regasification is used to convert the LNG back into its gas form, which enters the domestic pipeline distribution system and is ultimately delivered to the end-user.

Because LNG is sold in accordance with its BTU value, accurate analysis of the BTU value of any particular LNG shipment, as well as analysis of the constituent components of the LNG, as it is off-loaded from a respective tanker ship is crucial. For example, to determine an expected price for a particular shipment, when LNG is loaded onto a tanker ship at an overseas location, such as Trinidad and Tobago where large natural gas reserves are found, the supplier calculates the Btu value of the LNG as it is loaded into the hull of the ship. Additionally, because the Btu value of the shipment will likely change in transit, for example due to vaporization of some of the LNG while it is sitting in the hull of the ship, the recipient of the LNG shipment also desires to accurately determine the Btu value of the delivered LNG shipment. The operator of the tanker ship carrying the LNG shipment is also keenly interested in accurate BTU measurement of both the loaded LNG as well as the off-loaded LNG as the shipper typically burns the LNG vaporized in transit to run the ship and, thus, is responsible for cost of the LNG vaporized in transit.

Accordingly, it is desired to provide a method and system for accurately measuring the BTU value of an LNG shipment as it is off-loaded from a tanker ship.

One related art method that addresses the issue discussed above is disclosed in U.S. Pat. No. 3,933,030 to Forster et al. In Forster, a system is disclosed for the continuous monitoring of the density of cryogenic liquids, such as LNG. In accordance with the Forster system the dielectric constant of stored LNG is instantaneously determined by the use of sensors in the storage tank. Multiple sensors, each comprising a capacitor probe, are placed at various locations within the storage tank. The sensors are then operable to instantaneously measure the dielectric constant of the liquid within the tank and from this data the density of the liquid in the tank is determined. From the density measurement it is possible to then calculate the BTU per unit volume and appropriate charges per BTU can be calculated.

Several problems arise from a system such as the one disclosed in Forster, however. For example, the accuracy of the BTU measurement is unacceptable for today's standards.

Other, more recent, related art systems utilize chromatograph technology to determine the BTU value of LNG. These related art systems, however, also suffer from poor accuracy and/or high levels of maintenance. For example, one known system utilizes a method in which liquid gas is circulated in tubes that are submersed in a heated solution. The heat in the solution, in turn, heats the tubing which vaporizes the liquid gas. This method of vaporization is very inefficient, however, and the accuracy of any resulting BTU measurements are unacceptable, e.g., less than 5 BTU, that is, the swing on the BTU measurement is greater than 5 BTU.

Accordingly, it is desired to provide a system that does not suffer from at least these problems and which can provide a much more accurate and detailed assessment of liquefied gas and at the same time requires less maintenance than current systems.

IV. SUMMARY OF THE INVENTION

Illustrative, non-limiting embodiments of the present invention may overcome the aforementioned and other disadvantages associated with related art liquid gas vaporization and measurement systems. Also, the present invention is not necessarily required to overcome the disadvantages described above and an illustrative non-limiting embodiment of the present invention may not overcome any of the problems described above.

It is an object of the present invention to provide a novel system and method for efficiently and accurately sampling and measuring liquid gas.

To achieve the above and other objects an embodiment in accordance with the invention includes a system for vaporizing and measuring liquid gas, the system comprising a transmission device operable to transmit liquid gas, a measurement device operable to continuously extract at least a portion of the liquid gas from the transmission device while it is being transmitted by the transmission device, convert the extracted liquid gas from liquid form to vapor form and determine the constituent components of the vapor gas.

Another embodiment of the invention includes a device for sampling and vaporizing liquid gas, the device comprising a vaporizer operable to receive liquid gas at a first flow rate from an input port and convert the received liquid gas into vapor gas, an accumulator connected to the vaporizer and operable to receive and store the vapor gas, and a heated regulator connected to the accumulator and operable to receive stored vapor gas from the accumulator and control the pressure of the received vapor gas to be within a desired pressure range. In this exemplary embodiment stainless steel tubing is used to convey the gas throughout the system. Additionally, the tubing within the vaporizer has a diameter as small as one-eight inch and is spirally wound around one or more cartridge heaters to efficiently flash vaporize the liquid gas. A constant flow of gas through the system is also maintained by using a speed loop.

An even further embodiment of the invention includes a method of measuring the constituent components of liquid gas, the method comprising receiving the liquid gas into a vaporizing device, selectively directing the received liquid gas into a vaporizer within the vaporizing device, converting the liquid gas into vapor gas and accumulating the vapor gas in a relatively small storage device, for example, one-half cubic foot volume. The exemplary method further includes outputting the vapor gas accumulated in the storage device and directing the outputted vapor gas from the storage device to a measuring device operable to determine the constituent components of the vapor gas.

As used herein "gas" means any type of gaseous matter capable of pipe transmission, including natural gas, organic gases, industrial gases, medical gases, monomolecular gases, gas mixtures, and equivalents.

As used herein "connected" includes physical, whether direct or indirect, permanently affixed or adjustably mounted. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawings which are provided for illustration purposes as representative of specific exemplary embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

Given the following detailed description, it should become apparent to the person having ordinary skill in the art that the invention herein provides a novel liquid gas vaporization and measurement system and a method thereof for providing significantly augmented efficiencies while mitigating problems of the prior art.

V. BRIEF DESCRIPTION OF THE DRAWINGS

The aspects of the present invention will become more readily apparent by describing in detail illustrative, non-limiting embodiments thereof with reference to the accompanying drawings, in which.

VI. DETAILED DESCRIPTION OF ILLUSTRATIVE, NON-LIMITING EMBODIMENTS

Exemplary, non-limiting, embodiments of the present invention are discussed in detail below. While specific configurations and dimensions are discussed to provide a clear understanding, it should be understood that the disclosed dimensions and configurations are provided for illustration purposes only. A person skilled in the relevant art will recognize that, unless otherwise specified, other dimensions and configurations may be used without departing from the spirit and scope of the invention.

Figure 1:
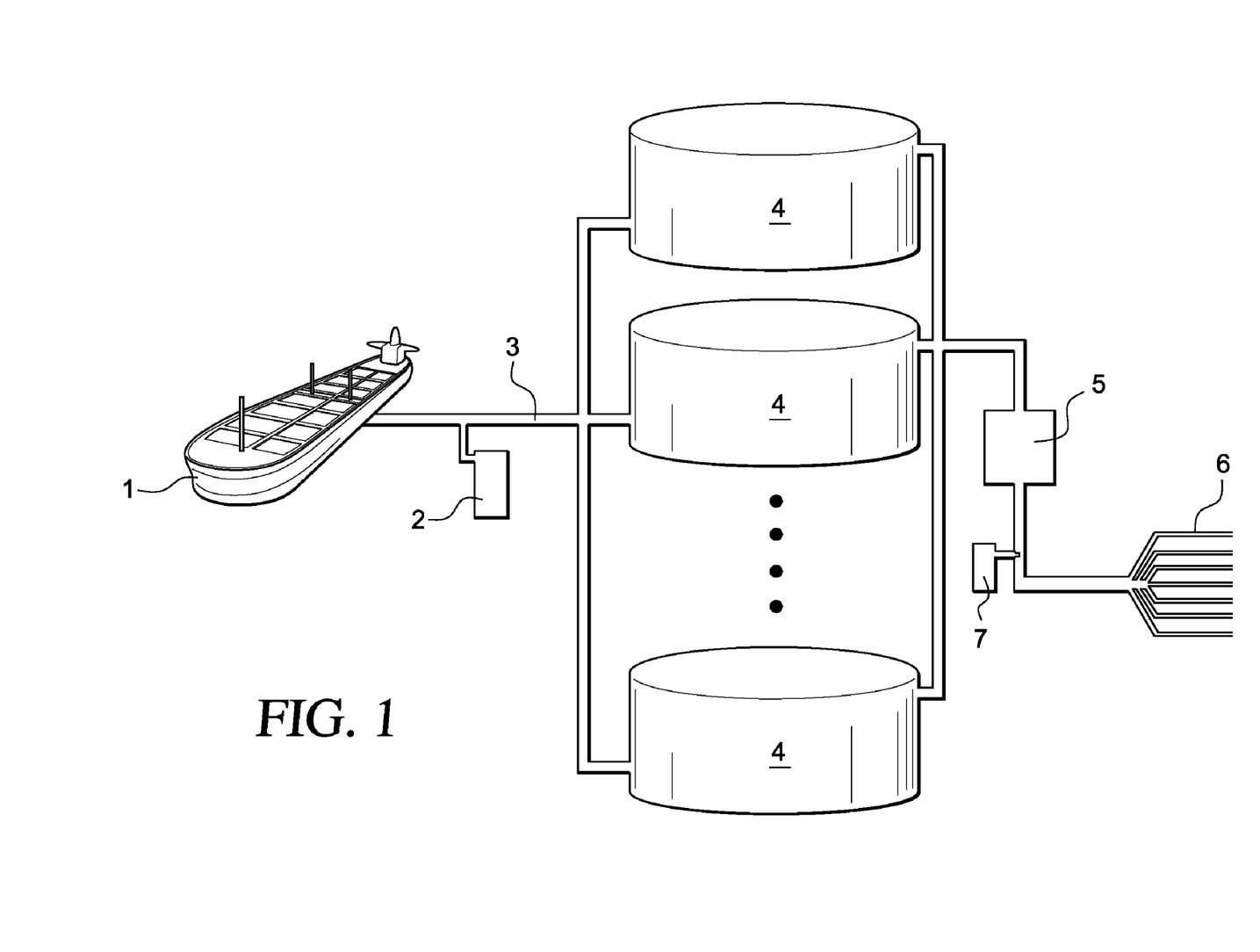
FIG. 1 is block diagram illustrating a system in accordance with the present invention.

FIG. 1 is an exemplary block diagram illustrating a system in accordance with the present invention. As shown, the system of FIG. 1 comprises a tanker ship 1 carrying a shipment of liquefied natural gas (LNG). In accordance with this embodiment, tanker 1 docks into a port where the shipment of LNG is to be off-loaded to storage tanks before being regassified and shipped to various gas customers. According to the present embodiment tanker ship 1 is a marine vessel. However, a skilled artisan would understand that tanker ship 1 could also be any vehicle or device capable of transporting or storing liquefied gas, such as a tanker truck or other storage device. To accurately measure the BTU value of the LNG being offloaded from tanker 1, a vaporizer unit 2 in accordance with the present invention and discussed in detail below, is connected in-line with the LNG being transferred from tanker 1 to storage tank 4 via, for example, pipeline 3. As LNG is transported in pipeline 3 to storage tank 4, at least a portion of the LNG is delivered to vaporizer unit 2 to be analyzed and measured.

As discussed in detail below, vaporizer unit 2 continuously receives an amount of LNG from pipeline 3, vaporizes the LNG into gaseous form and analyzes the vaporized LNG to very accurately determine the constituent components of the gas, for example, via a chromatograph. Thus, on a continuous basis, that is, continually as the LNG is being transported in pipe 3 to storage tank 4, the real-time, or at least very near-real-time, BTU value for the LNG being transported is calculated. Accordingly, an accurate accounting of the LNG and its BTU value and/or cost is determined for the LNG being offloaded or otherwise transferred into storage tank 4. It should be noted that not only is the placement of the vaporizer unit 2 important for such calculations, e.g., the LNG vaporizer unit 2 should be as close to the LNG discharge line as possible, but also the structure and configuration of the vaporizer unit additionally contributes to extremely accurate calculations of the BTU value of the LNG.

The LNG from which the representative sample is extracted and used in unit 2 is pumped or otherwise transferred into storage tank 4 where it is kept at the appropriate pressure and temperature to reduce both the risk of explosion as well the risk of inadvertent vaporization into the atmosphere. The LNG resides in tank 4 until it is needed, e.g., in the form of natural gas vapor for consumers, upon which time the LNG is pumped from tank 4 and regassified, or vaporized, by degasification device 5. Degasification or vaporization device 5 can be any one or combination of known vaporization devices. For example, vaporization device 5 can be an open rack vaporizer (ORV), a submerged combustion vaporizer (SCV), a combined heat and power unit with SCV (CHP-SCV), an ambient air-heated vaporizer or any combination of these or other types of vaporizers.

After the bulk-stored LNG for consumption by consumers has been converted into vapor gas, the vapor gas is transferred, for example, via a pipeline system 6, to local distributors, i.e., the LCDs, and to the end-users. At any point after the LNG has been turned back into gas by vaporization device 5, the gas can be, but in accordance with the invention does not have to be, sampled and conditioned via a Gas Sample Conditioning System 7 such as the one disclosed in U.S. patent application Ser. No. 11/169,619, which assigned to the same assignee as the present invention.

Figure 2:
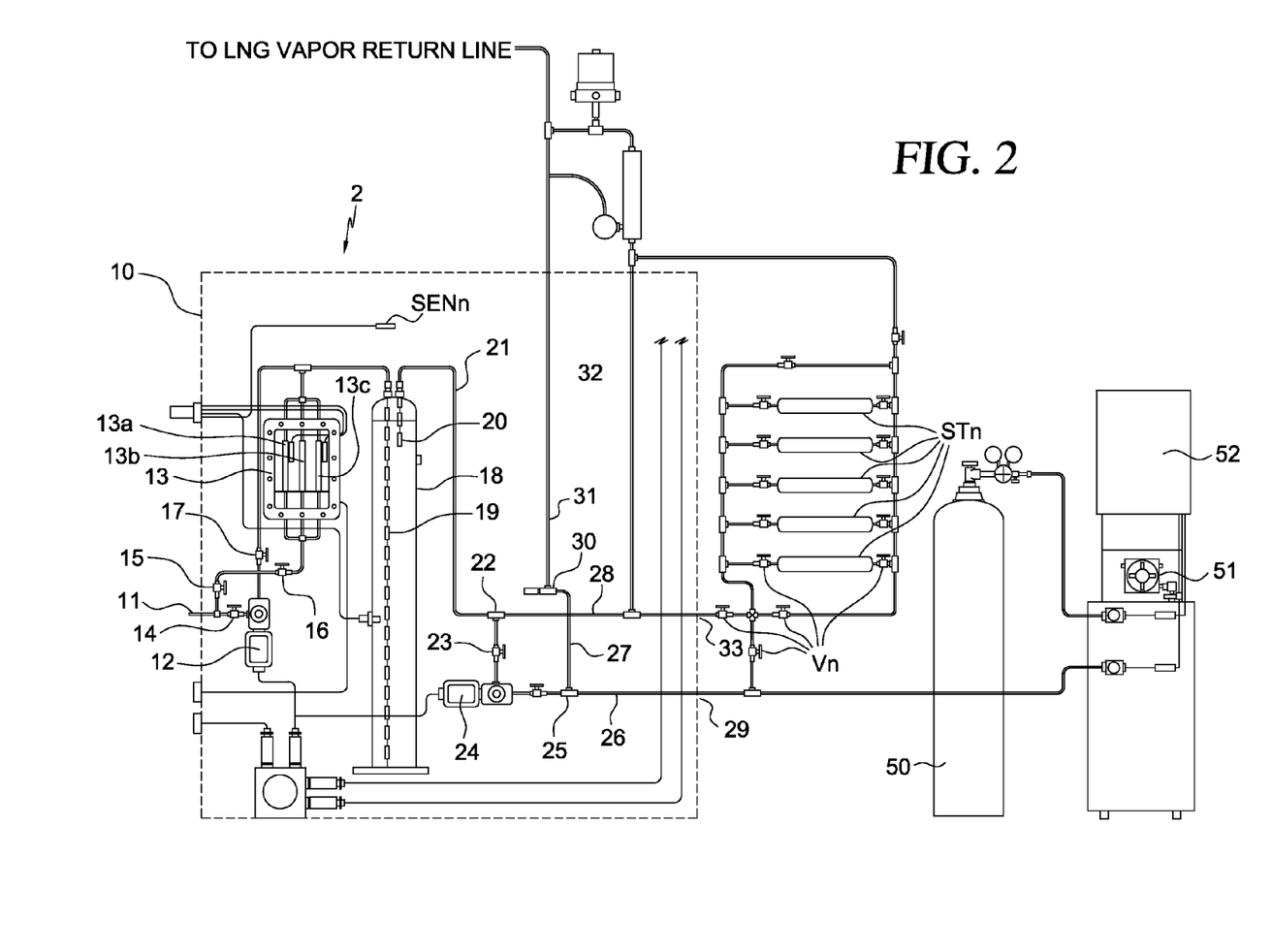
FIG. 2 is a schematic diagram of a vaporizing and measurement device in accordance with the present invention.

FIG. 2 is a schematic diagram of an LNG vaporizer unit 2 in accordance with the present invention. In accordance with the exemplary embodiment of vaporizer unit 2 shown in FIG. 2, LNG is input to cabinet 10 via LNG inlet port 11 which comprises, for example, stainless steel tubing having a diameter of ¼-inch. Cabinet 10 comprises an enclosure for providing protection from the elements, such as rain, snow, ice, wind, etc. to the individual components within. Inlet port 11 is connected to ¼ inch tubing within enclosure 10 which, in turn connects to first and second vaporizer stages 12, 13, respectively. The first and second vaporizer stages 12 and 13 operate independently to vaporize LNG into its gaseous form. In particular, LNG enters inlet port 11 in liquid form at a temperature of approximately −249° F., although a person of ordinary skill in the art would understand that LNG remains in liquid form at temperatures generally below 10020 F. and, thus, consistent with the invention other temperatures are possible as well. The LNG input to inlet port 11 is then selectively channeled to one or both of the first and second stage vaporizing devices 12, 13.

Because LNG begins to vaporize as soon as it begins to heat up and the longer a tube carrying LNG is, the warmer the LNG gets, the tubes carrying the LNG within enclosure 10 and connecting the various devices within the vaporizer unit 2 are kept as short as possible, i.e., to minimize the amount of vaporization that takes place prior to the LNG entering one or both of the first and second stage vaporizing devices 12, 13. Also, insulation, such as two inches of polyisocyanate insulating material, is placed on and around the ¼ inch tubing that carries the LNG from the input port to each of the first and second stage vaporizer devices.

Valve 14 is attached to ¼ inch tubing that connects the inlet port 11 to first stage vaporizer 12. Valve 14 operates to shut-off or open the path for LNG to flow into the first stage 12. The first stage vaporizer 12 uses a heated spiraled entry (not shown) as well as exiting heat transfer and the gas output exits at approximately 10020 F. at a flow rate of 18 SCFH (standard cubic feet per hour).

As gas exits the first stage vaporizer 12 it travels through ¼ inch tubing to the top of accumulator device 18. Accumulator device 18 is a gas cylinder capable of storing natural gas vapor.

The second stage vaporizer 13 is connected to the inlet port 11 via additional ¼ inch tubing and one or more valves 15, 16. The second stage vaporizer 13 comprises a plurality cartridge heaters 13a, 13b, 13c around each of which is wound a length of ⅛ inch tubing. For example, as shown in FIG. 2, three cartridge heaters each have respective lengths of ⅛ inch tubing wound around their outer surface. The tubing around each of the heaters is connected to the ¼ inch tubing carrying the LNG to the stage 2 vaporizer.

It should be noted that valves 14-17, ideally, are suitable for cryogenic operation due to the low temperatures of the LNG flowing therethrough. Accordingly, valves 14-17 are optional and not necessarily required for the operation of the LNG cabinet.

Figure 3:
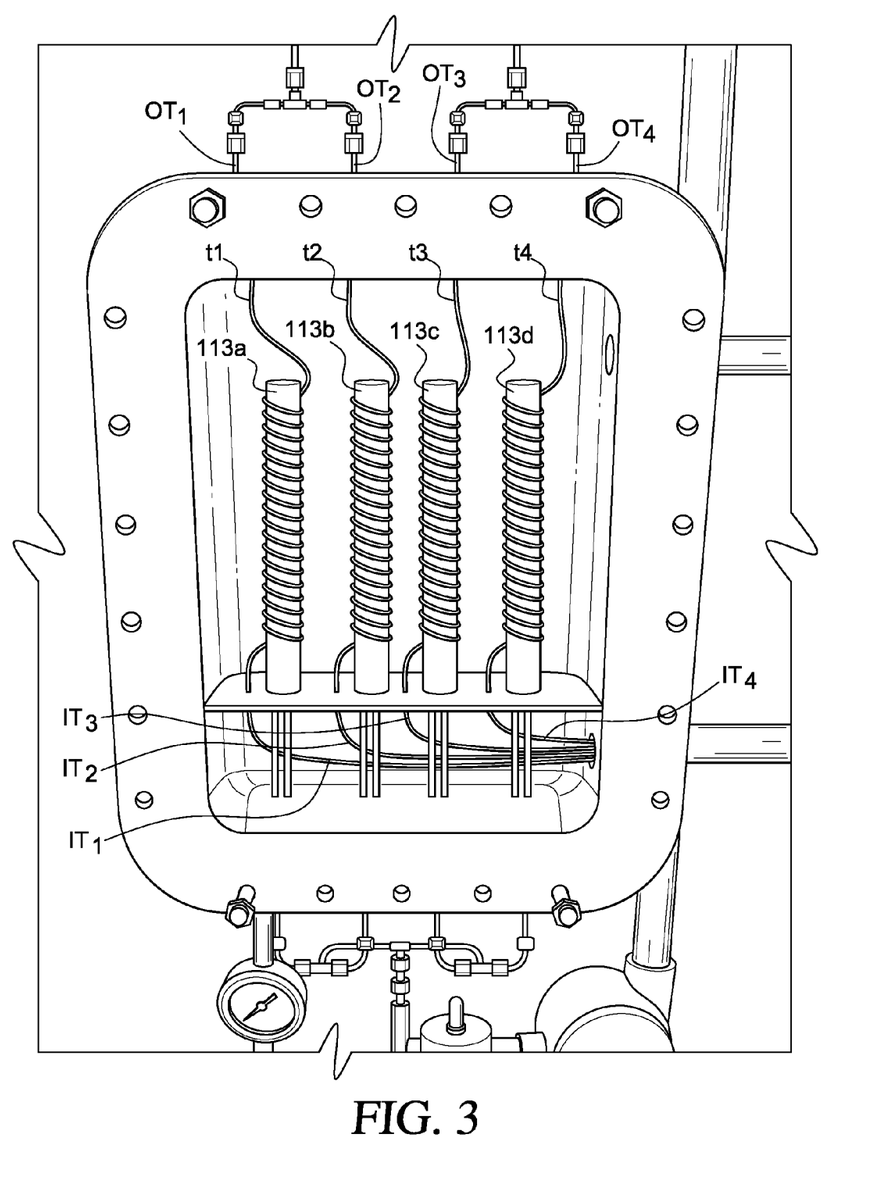
FIG. 3 is a drawing of an embodiment of a second stage vaporizer according to the invention.

FIG. 3 is a close-up view of an exemplary second stage vaporizer similar to second stage vaporizer 13 shown in FIG. 2. The second stage vaporizer shown in FIG. 3 utilizes four cartridge heaters 113a through 113d, as opposed to the three cartridge heaters shown in regard to the embodiment of FIG. 2. Otherwise, the second stage vaporizer shown in FIG. 3 is identical to the one depicted in FIG. 2. Also, as shown in FIG. 3, a respective length of ⅛ inch tubing t1-t4 is wound around each cartridge heater 113a-113d.

Referring to FIG. 3, the LNG enters the second stage vaporizer at the bottom via four respective ¼ inch input tubes $IT_1$-$IT_4$. Within the second stage vaporizer the LNG is then directed into four respective ⅛ inch tubes, t1-t4. Each tube t1-t4 is wound spirally around a respective cartridge heater 113a-113d that quickly heats the LNG within the narrow spiral tubing converting the LNG within the tubes to vapor gas. The vapor gas from each of the respective ⅛ inch tubes is then directed into a respective output tube $OT_1$-$OT_4$ and the vapor gas is directed into the accumulator in similar fashion as discussed with respect to FIG. 2.

Referring back to FIG. 2, respective valves (not shown) control the flow of LNG into the respective tubing wound around each of the cartridges 13a, 13b and 13c. In particular, the flow into each of the ⅛ inch tubes is controlled such that the total flow of LNG in the ¼ inch tube flows through the three ⅛ inch tubes in any combination, e.g., ⅓ in each of the three ⅛ inch tubes, ½ in each of two ⅛ inch tubes and none in the third ⅛ inch tube, etc. Further, it should be noted that valves 14-17 are also configured such that the LNG that enters the input port 11 can be directed in any desired percentage to both the first and second stage vaporizers 12 and 13. For example, it is possible to direct any amount, X, (where X=0% to 100%) of the LNG entering port 11 into the first or second stage vaporizer and an amount Y (where Y=100−X) into the other of the first and second stage vaporizers. Accordingly, it is possible to run the vaporizer cabinet 10 even if one of the first or second stage vaporizers should fail.

It should also be noted that even though the present embodiment includes three cartridge heaters, e.g., 13a, 13b and 13c, the invention is not limited to this configuration. One of ordinary skill would know that provided sufficient LNG/vapor flow through the second stage vaporizer, any number of cartridge heaters can be used.

As vapor gas exits the second stage vaporizer 13 the vapor gas is carried by ¼ inch tubing to accumulator 18. As shown, the vapor gas enters accumulator 18 at the top and is carried via a tube 19 inside the accumulator to an interior location within the tank 18. As vapor gas exits the tube 19 it is directed toward the inside wall of the tank 18. As the vapor gas impinges the interior wall of tank 18 it is mixed thoroughly with any gas already existing within the tank. Tube 19 is of variable length and can expel vapor gas within tank 18 at any height within the tank. However, in accordance with the present embodiment, the output of tube 19 is approximately 80 to 90 percent down toward the bottom of the tank.

Thoroughly mixed vapor gas within accumulator tank 18 is removed via additional tubing 20 near the top of tank 18. The removed gas is carried in ¼ inch tubing 21 to a "T" joint 22. At "T" 22 the vapor gas is either directed into tubing 28, through valve 23 or some combination of both. Valve 23 controls the amount of vapor gas permitted to flow into vaporizer stage 3 (ref. no. 24). Vaporizer stage 3 essentially operates as a pressure reducer. That is, stage 3 (24) controls the pressure for vapor permitted to enter tube 26, which carries the sample vapor gas to a chromatograph, discussed later. For example, in accordance with one scenario, vaporizer cabinet 10 is positioned in close proximity to a pipeline header carrying LNG from a tanker ship to on or more storage tanks (See, e.g., FIG. 1). As the storage tank 4 begins to fill with LNG the pressure within pipe 3 must increase in order to continue to fill tank 4. As the pressure in pipe 3 increases, so does the pressure in the sample line to cabinet 10 and through the various stages of vaporization. Accordingly, stage 3 (24) operates to control the pressure of vapor gas into tube 26. For instance, the pressure in tube 21 and through valve 23 might be somewhere around 10-65 PSI. Pressures in this range are typically detrimental to chromatograph devices and, thus, stage 3 reduces the pressure to an acceptable level, such as 5-10 PSIG. Vapor gas at an acceptable pressure is then output from cabinet 10 at port 29.

According to the embodiment shown in FIG. 2, a tube 27 is connected to a "T" joint 25 which is further connected to tube 26. Tube 27 is further connected to a relief valve 30 which releases vapor gas therethrough in the event the pressure in tube 26 should exceed a predetermined maximum value. That is, relief valve 30 normally does not permit gas to flow through it when the pressure in tube 26 is below a certain value. If, however, the pressure in tube 26 exceeds this value, relief valve 30 opens and releases an amount of gas necessary to reduce the pressure in tube 26 to below the predetermined value. Any vapor gas released by relief valve 30 goes through one-way valve 31 and is provided to an LNG vapor return line via tube 32.

Any vapor gas outputted from accumulator 18 that does not pass through valve 23 and into stage 3 (24) enters tube 28 and exits cabinet 10 at port 33. One or more valves, $V_n$, are provided to control gas flowing into sample tanks $ST_n$. For example, one or more sample tanks (e.g., ST1-ST5) are provided to store samples of vapor gas withdrawn from accumulator 18. For instance, different samples can be taken and stored at different times, such as at various times during the overall unloading process of a load of LNG from a tanker ship as it is transferred into a storage tank. Valves $V_n$ are individually opened or closed in order to store samples in sample tanks $ST_n$ at appropriate times.

The gas stored in any one of the sample tanks STn can be controlled to come directly from the output of accumulator 18 or it can be a sample taken from the output of vaporizer stage 3 (24). For example, during periods when a tanker ship is not being off-loaded, the LNG being inputted to input port 11 is recirculated LNG from a storage tank, such as tank 4 shown in FIG. 1. By recirculating LNG from storage tank 4 in this manner, a constant pressure (and temperature) is maintained in the lines of vaporizer 10. Because the pressure in the main line 3 is not significantly altered, as compared to the situation when a tanker is being off-loaded as described above, it is not necessary to regulate, or reduce, the pressure using stage 3 (24).

Thus, under these circumstances sample LNG is vaporized by one or more of stages 1 and 2 (12 and 13 in FIG. 2), vapor is collected and mixed in accumulator 18 and the vapor is drawn off through tubes 21 and 28 and out cabinet 10 through port 33. The vapor from the recirculated LNG sample is then directed to either sample tanks STn, bypassed around sample tanks STn and returned to the LNG vapor return line or channeled through one of the valves Vn and into chromatograph 52 via optional liquid block 51. For example, optional liquid block 51 is used for natural gas production gas where liquids are typically present. Similarly, if desired, by opening or closing the appropriate combination of valves Vn, the vapor gas outputted from stage 3 (24) is directed to the sample tanks STn, bypassed around sample tanks STn and returned to the LNG vapor return line or channeled through one of the valves Vn and into chromatograph 52 via optional liquid block 51.

In order to calibrate chromatograph 52, a tank of calibration gas with a known composition is stored in cal tank 50. Accordingly, when it is desired to calibrate the chromatograph 52, the vapor gas outputted from cabinet 10, through either port 29 or port 33, is shut-off automatically and calibration gas from tank 50 is applied to the chromatograph 52.

While various aspects of the present invention have been particularly shown and described with reference to the exemplary, non-limiting, embodiments above, it will be understood by those skilled in the art that various additional aspects and embodiments may be contemplated without departing from the spirit and scope of the present invention.

Figure 4:
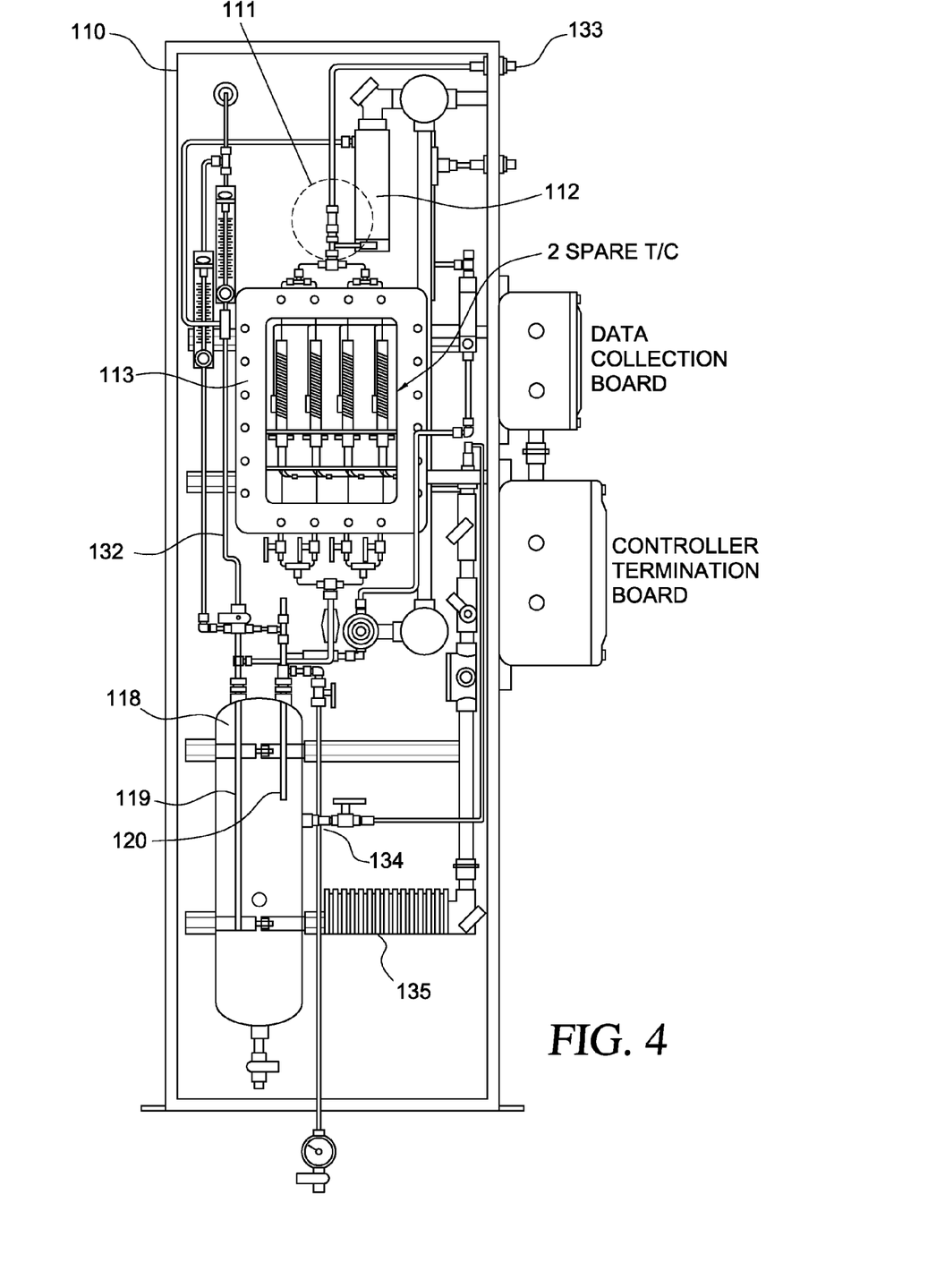
FIG. 4 is a drawing of an alternative embodiment according to the invention.

For example, FIG. 4 illustrates and alternative embodiment of a vaporizer cabinet which differs somewhat from vaporizer 2 shown in FIG. 2. The vaporizer shown in FIG. 4 is similar in most respects to the vaporizer shown in FIG. 2. However, the embodiment of FIG. 4 uses a four-cartridge heater similar to the one illustrated in FIG. 3 and various other components are configured differently.

In particular, as shown in FIG. 4, LNG is input to the vaporizer cabinet 110 through inlet port 11 located near the top of the cabinet 110. A first stage vaporizer 112 receives a portion of the LNG and a second stage 113 receives the balance of the LNG. It should be noted that the pipe lengths for the pipes bringing LNG into the cabinet from the header pipe 3 (FIG. 1) are kept as short as possible to minimize any heating of the LNG within the inlet pipes. The second stage vaporizer 113 utilizes four cartridge heaters as shown in FIG. 3. Both the first and second stages heat the LNG and convert it to vapor gas which is accumulated in accumulator 118. Also, connected to each of the first and second stages, 112 and 113, as well as the accumulator 118, is tubing 132 that exhausts from the cabinet 110 at outlet 133 to an LNG vapor return line (not shown). Heater 135 is located within the LNG vaporizer cabinet to keep the outlet tubes at or above a minimum temperature, for example, such that the gas within the outlet tubes remains in gaseous form.

Additionally, with respect to the embodiment shown in FIG. 4, the system pressure is monitored, as opposed to monitoring the pressure into the chromatograph, as is the case in regard to the embodiment of FIG. 1. In particular, vapor pressure is sampled at approximately the middle of accumulator tank 118. The vapor is removed through port 134 and the pressure is measured. Accordingly, by monitoring the system pressure data is provided with respect to the unloading pump sequences, pressures and pump failures, for example, as the LNG is being pumped from tanker 1 (FIG. 1). Also, in the embodiment of FIG. 4, the speed loop vapor, i.e., used to maintain a constant flow through the system, as discussed above with respect to the embodiment of FIG. 1, is taken from the discharge port of the accumulator tank 118 in order to promote a more fully mixed sample.

Modifications to the embodiments of FIGS. 2 and 4 can been made to even more closely monitor the system pressure. For instance, during tanker offloading, for example from tanker 1 (FIG. 1) into storage tanks 4, the BTU value calculations are affected by things, such as changes in tanker pump pressure and variations in storage tank filling levels. Specifically, events such as these change the speed loop flow rate which, in turn, can affect the value of the BTU calculation. Thus, by carefully monitoring and controlling the flow rate in the speed loop, these types of anomalies are detected and accommodated.

It has also been recognized that when one or more of the tanker pumps suddenly begin pumping, or otherwise change their pump rate, the BTU value reading is also affected in similar fashion to that mentioned above. Accordingly, in accordance with a further embodiment, an additional device can be added within the LNG cabinet to assist in controlling the flow rate. For example, a flow controller, such as a Brooks 5850i Mass Flow Controller from Brooks Instrument of Hatfield, Pa., can be included within the LNG cabinet to control the flow rate within the speed loop. The location of the flow control device within the speed loop is not critical. However, one viable location is, for example, on tubing 21 at the output of accumulator tank 18.

Figure 10:
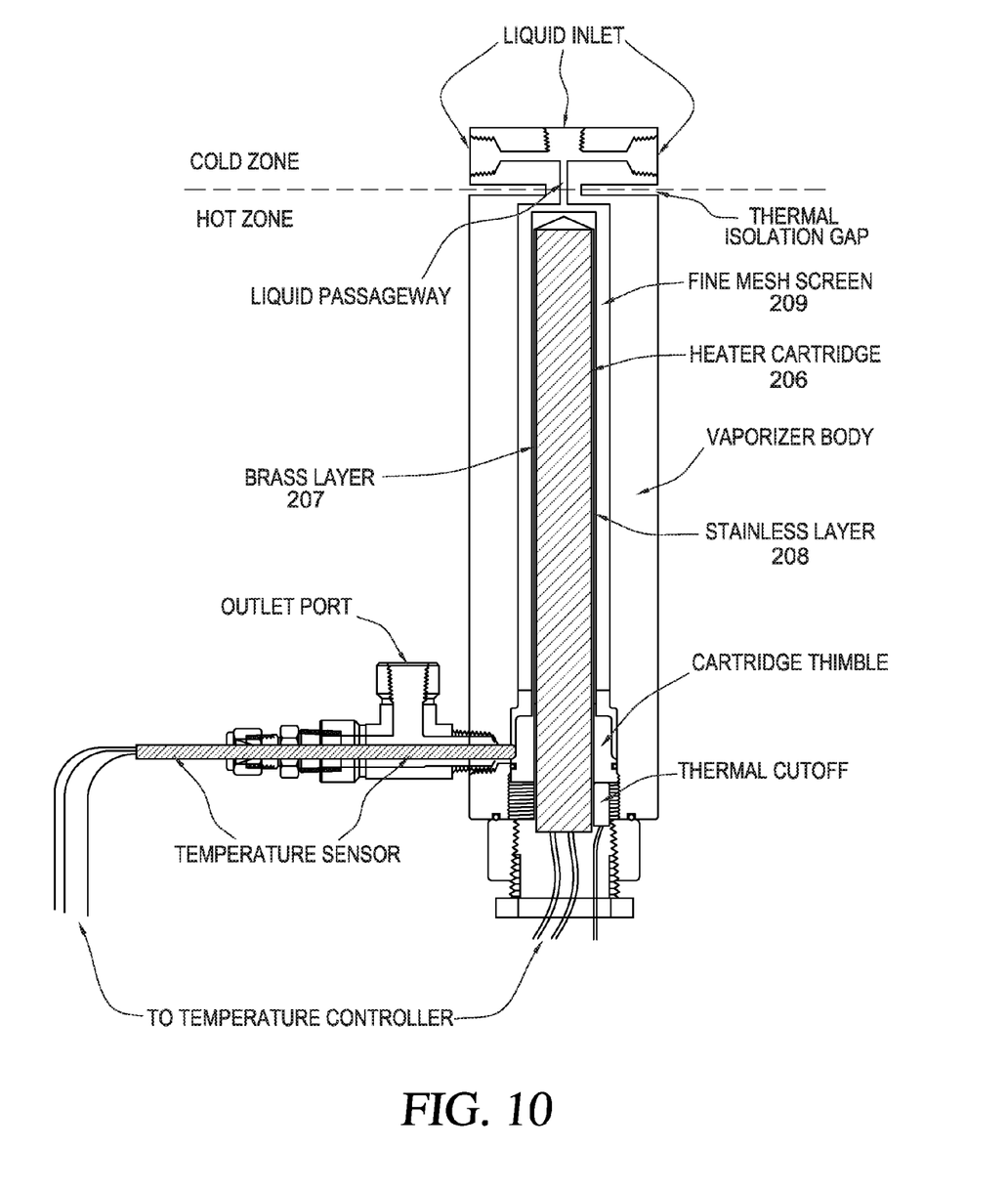
FIG. 10 is a schematic diagram of a single path vaporizer according to the invention.

The first stage vaporizer may be a multi-path vaporizer comprising, for example, 3 vaporizer coils or 4 vaporizer coils to allow a 25% surplus heating capacity. However, as illustrated in FIG. 10, the vaporizer 205 may comprise a single path having a diameter of about 2½ inches and a length of about 10 inches to fully vaporize the liquid. The single path vaporizer is designed so the liquid enters the top of the vaporizer (e.g., at about −260 degrees F.) and cascades via a mesh screen 360 degrees around a heater inner chamber, and gas exits via a port disposed at the bottom (e.g., at about 120 degrees F.), thereby minimizing disproportionate accumulation of heavies in the vaporizer. The single path vaporizer may comprise an inner heater cartridge 206, a first metal layer 207 (e.g., brass) surrounding the inner heater cartridge to promote uniform heating and eliminate hot spots, a second non-reactive metal layer 208 (e.g., stainless steel) surrounding the inner heater cartridge, and a mesh layer 209.

In certain embodiments, the system according to the present invention may comprise two vaporizers, a first stage vaporizer 12 being on the main incoming product line prior to the second stage vaporizer (primary vaporizer) 13, as illustrated in FIG. 2. However, the first stage vaporizer may remove light hydrocarbon components (lights) from the liquid sample and therefore the liquid entering the primary vaporizer may not include some components, thereby resulting in an inaccurate or incorrect analysis by the gas chromatograph 52.

Figure 5:
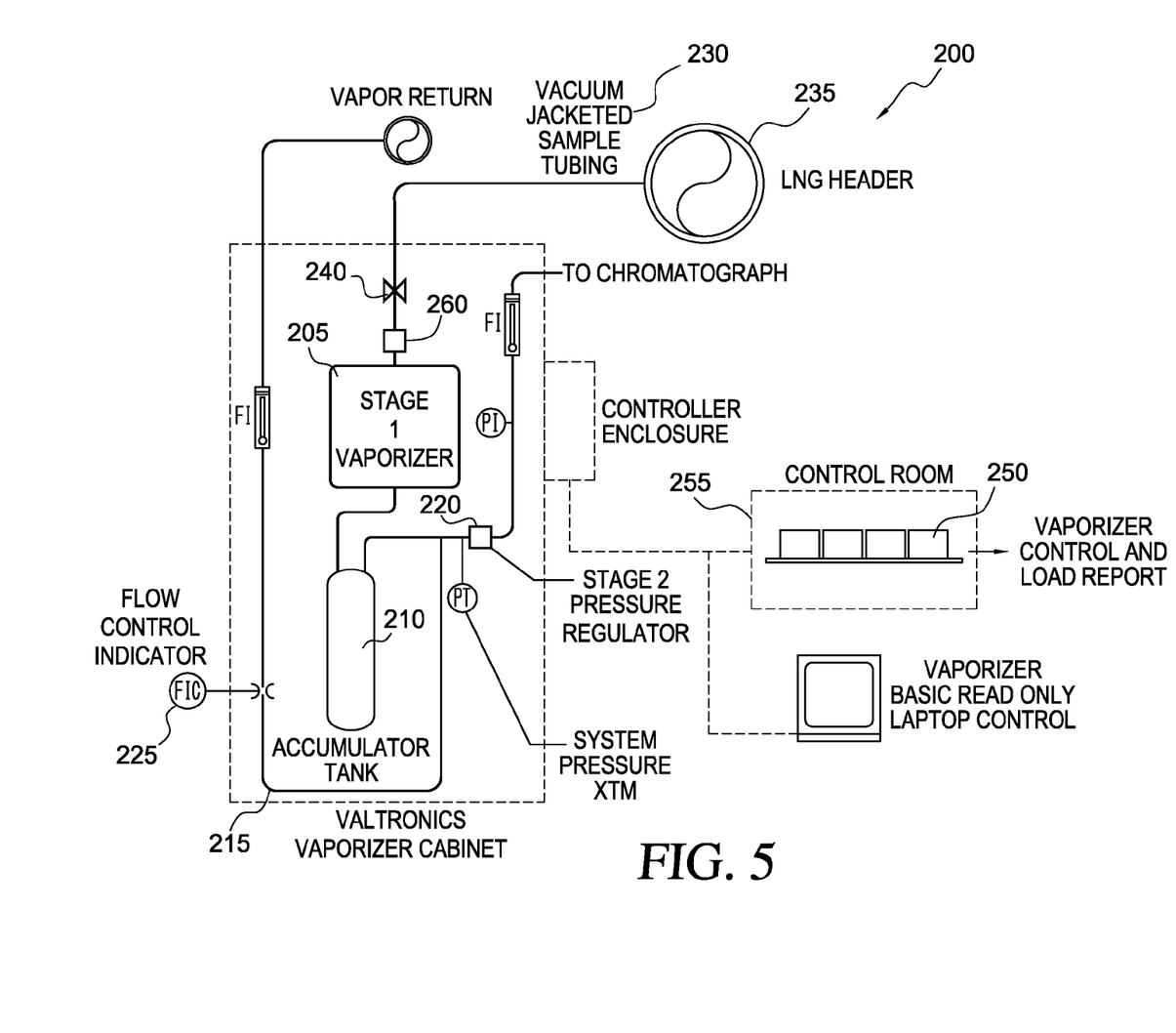
FIG. 5 is a schematic diagram of an alternative embodiment according to the invention.
Figure 6:
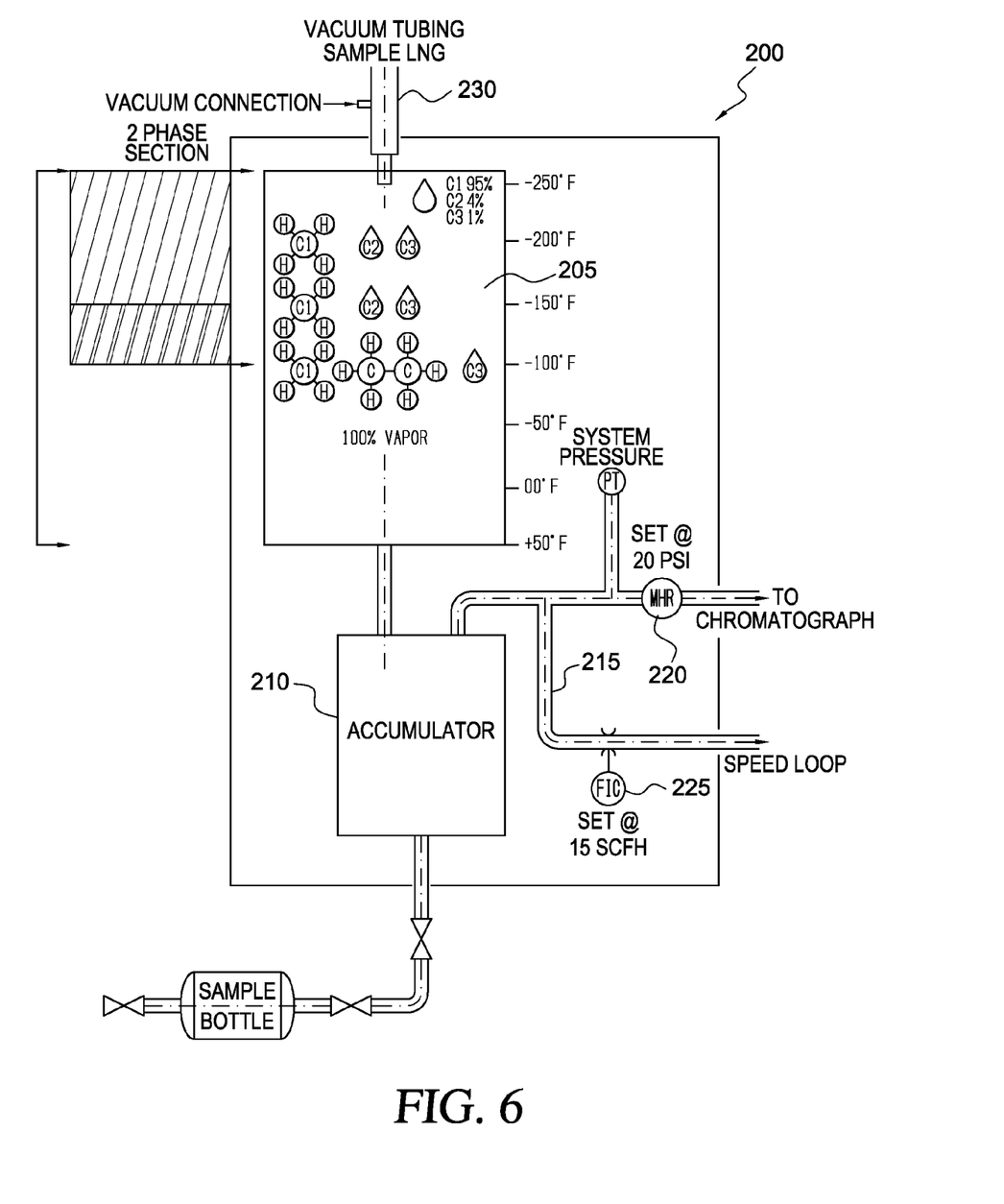
FIG. 6 is a schematic diagram of an alternative embodiment according to the invention.
Figure 7:
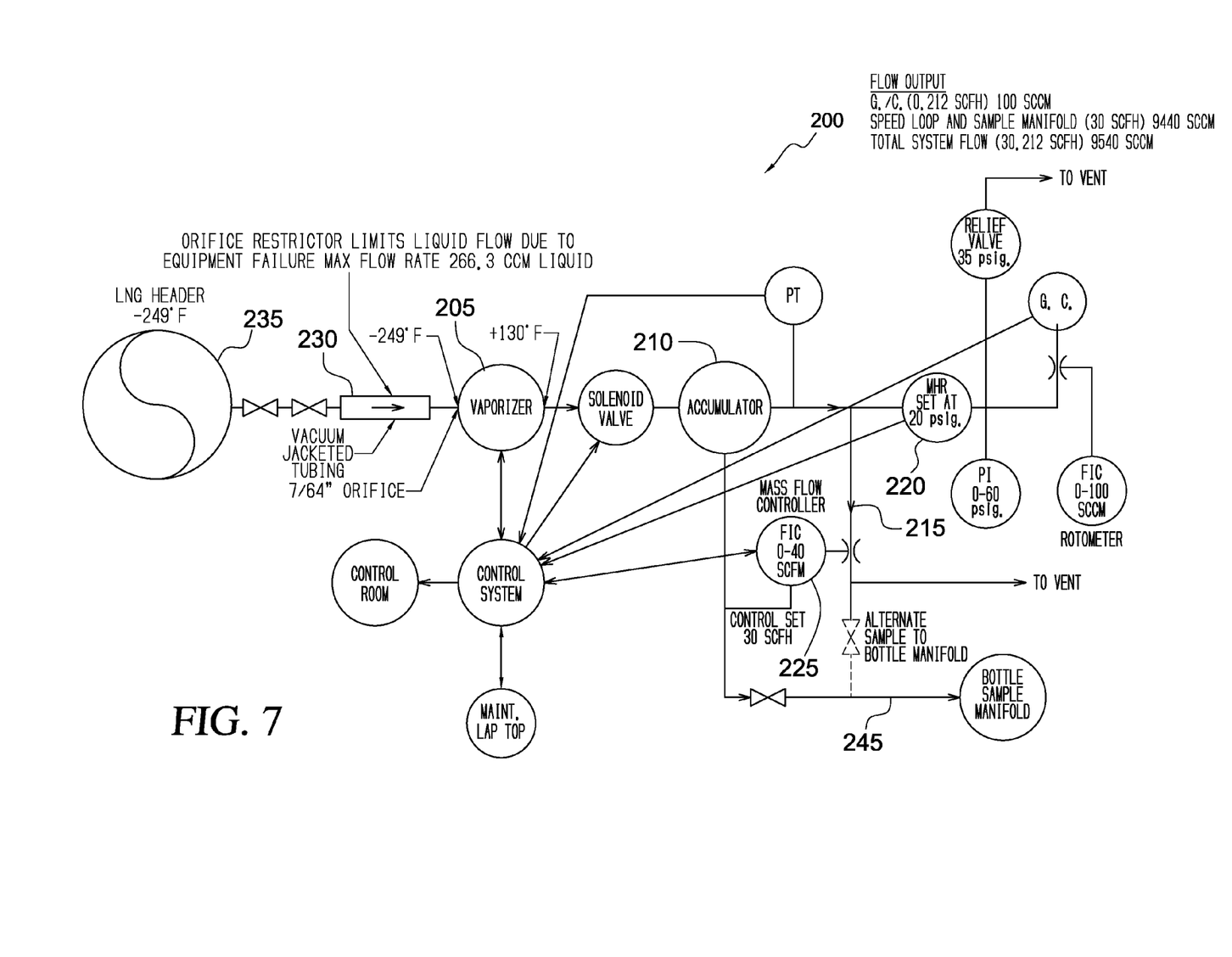
FIG. 7 is a process flow diagram of an alternative embodiment according to the invention.

Removing the first stage vaporizer mitigates this issue, but causes another problem (i.e., an extended analysis cycle time). To overcome this problem, a speed loop may be installed downstream of the accumulator tank prior to a heated regulator, as depicted in FIG. 5, FIG. 6, and FIG. 7. The speed loop comprises the connections between the accumulator 210 and the heated regulator 220. This configuration ensures a fresh sample is available each time one is needed for analysis. FIGS. 5-7 show a system 200 according to an alternative embodiment of the present invention in which the first stage vaporizer (12 in FIG. 2) is removed. Thus, the second stage (primary) vaporizer 205 is Stage 1; the accumulator 210 is Stage 2, a vapor bypass control loop 215 is Stage 3, and a heated pressure regulator 220 is Stage 4.

By controlling the flow through the vaporizer and by keeping it consistent, a more stable analysis is achieved. In certain embodiments, manual control valves may perform this task. However, due to variations in pressure, constant adjustment of manual valves may be required. In other embodiments, to compensate for inlet pressure variation, a thermal mass flow meter 225 with built in control valve and PID (proportional-integral-derivative) controller may be utilized in the vapor bypass control loop 215. The controller receives the input from an onboard RGC unit. As illustrated in FIG. 5, a rotometer(s) may be incorporated in the vapor pathway.

It is known that some facilities recirculate product through process lines at a lower or higher pressure than normal operating pressure. When the pressure changes, the flow through the vaporizer changes, thereby resulting in an incorrect analysis. By adding the vapor bypass control loop 215, the problem is overcome by keeping constant back pressure on the vaporizer 205 during pressure changes (increasing and/or decreasing).

Figure 8:
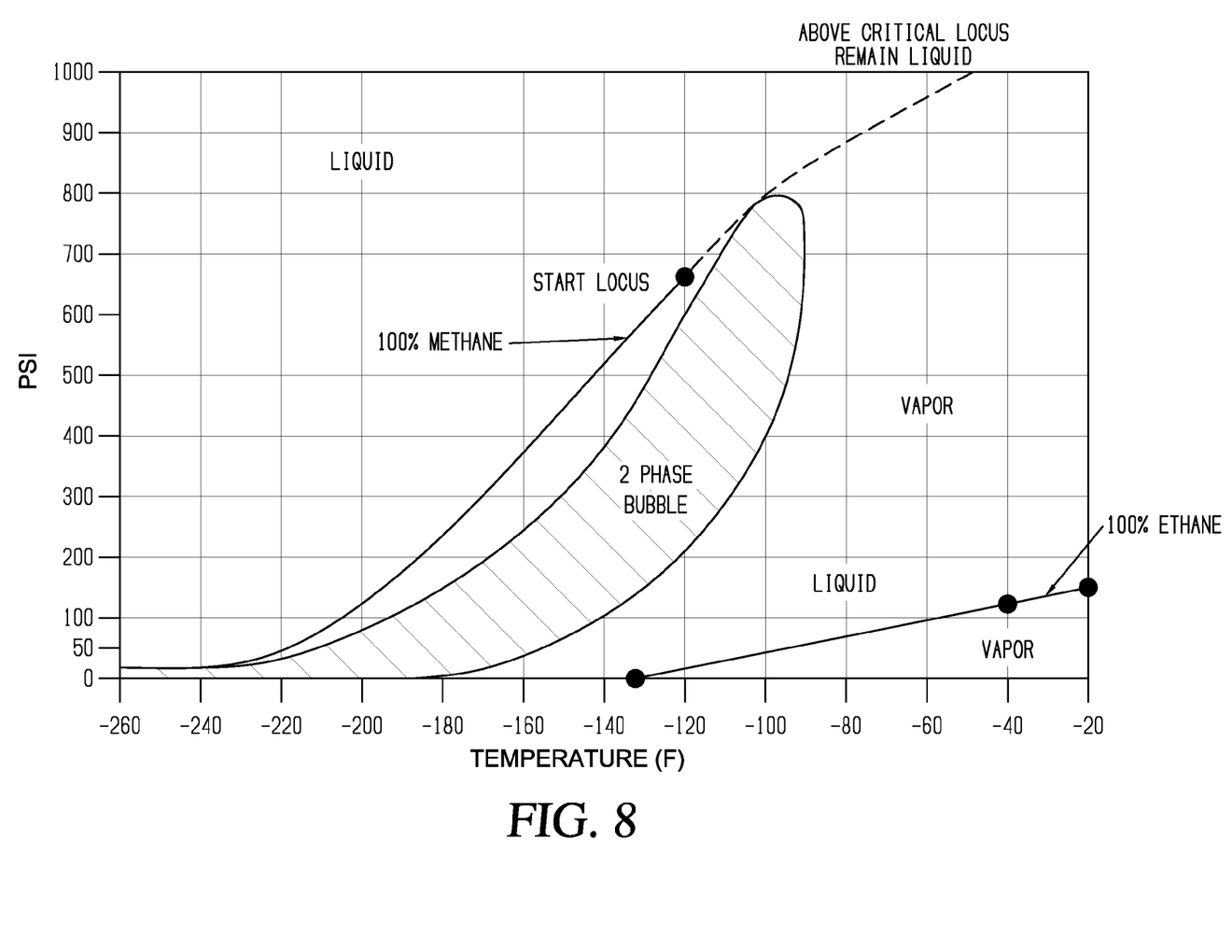
FIG. 8 is a liquid-vapor phase diagram for a 92.5% methane and 7.5% ethane mixture.

It is desirable to make sure the temperature of the liquid sample is maintained to the point of entry into the vaporizer. This was found to be critical as any warming during transportation results in pre-vaporization/flashing of the product prior to flowing through the vaporizer. As a result, product components (lights, intermediates, and heavies) may separate and enter the vaporizer at different times, resulting in faulty analysis by the gas chromatograph. For example, FIG. 8 shows a liquid-vapor phase diagram a mixture of 92.5% methane and 7.5% ethane having a two-phase bubble which the present invention seeks to avoid prior to the vaporizer.

Insulation or preferably vacuum-jacketing 230 of the tubing from sample point, LNG header, 235 to vaporizer 205 may be used to prevent or minimize such pre-vaporization/flashing. For example, In certain embodiments, the vacuum jacketing may comprise a ¼ inch process tube inside a 1½ inch outer tube with a zero vacuum pulled and sealed. To decrease lag time, the standard ¼ inch process tube inner diameter (ID) may be decreased to about 3.05 mm to decrease the volume inside the process tube. A flow restrictor 240 (FIG. 5) may be installed at the entry of the vaporizer 205 to assist in even flow through the unit resulting in a better sample analysis by the gas chromatograph.

Figure 9:
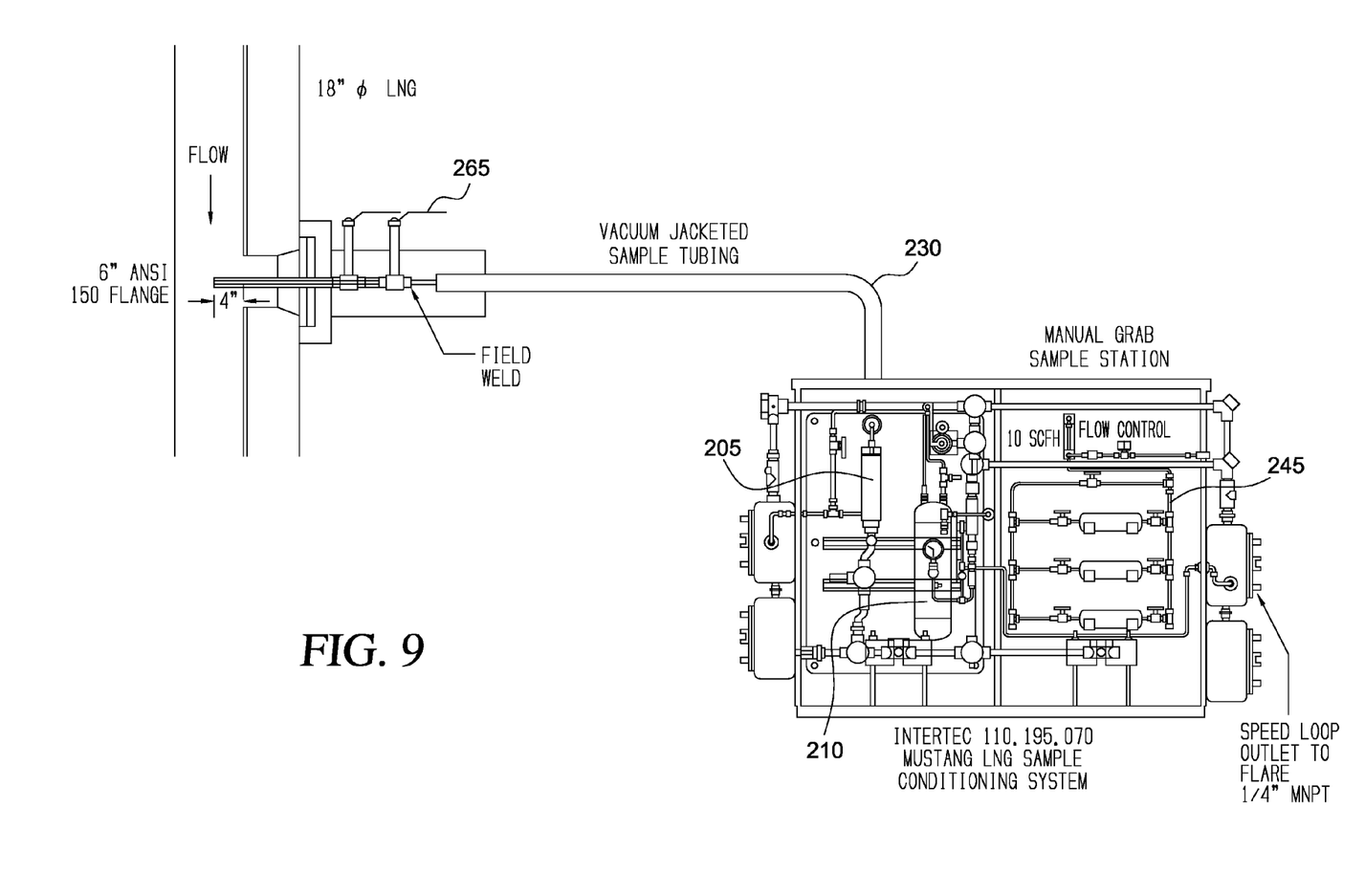
FIG. 9 is a schematic diagram of an alternative embodiment according to the invention.

The filling of sample tanks or cylinders STn may disturb the desired flow characteristics to the gas chromatograph and the flow through the vaporizer when sample takeoff occurs after the accumulator and before the heated regulator. Accordingly, changing the filling 245 of sample tanks to the exit of the vapor bypass control loop and/or at the exit of the accumulator, as shown in FIG. 7 and FIG. 9, prevents interruption of the flow through the vaporizer and/or to the gas chromatograph.

As depicted in FIG. 2, an impingement tube 19 having a series of holes spaced at predetermined intervals has been found to provide an increased stable vapor sample by promoting admixing within the accumulator tank (accumulator/mixing tank). An extraction tube 20 (which may protrude into the accumulator tank about 6 inches) to ensure heavies which may partition to the inner wall of the accumulator are not being removed also resulted in an increased stable analysis. Also during normal operation (flow through the system), when the cabinet door is opened, ambient air is introduced into the enclosure which may adversely impact the accuracy of the analysis by the gas chromatograph. This may be prevented by insulating the accumulator tank.

In certain embodiments, a microprocessor-based auto-tuner 250 may be added to the heater control board 255, as shown in FIG. 5. Without auto tuning, the lag time in standard controllers may result in uneven firing of the vaporizer heaters, resulting in uneven vaporization of the liquid product.

Furthermore it may be desirable to include in certain embodiments, a temperature sensor 260 may be added to the input of liquid at the vaporizer 205 (FIG. 5). The temperature sensor 260 allows tracking of the process input temperature to ensure no pre-vaporization/flashing of the product prior to entry into vaporizer. This input is monitored by software, logged, and is capable of set point alarms.

A further modification of the invention contemplates inclusion of a cryogenic shut off valve 265 outside of the vaporizer cabinet to permit shut off the process liquid on the loss of power and/or vaporizer heater failure to prevent liquid from flowing through at least one of the accumulator, heated regulator, vapor bypass, or thermal mass flow meter which could result in an unsafe condition and will cause damage to the equipment.

It would be understood for a person having ordinary skill in the art that a device or method incorporating any of the additional or alternative details mentioned above would fall within the scope of the present invention as determined based upon the claims below and any equivalents thereof.

Other aspects, objects and advantages of the present invention can be obtained from a study of the drawings, the disclosure and the appended claims.

What is claimed is:

1. A system for vaporizing and measuring liquid gas, comprising: a transmission device to transmit liquid gas; a vaporizer to receive a first amount of liquid gas and convert the first amount of liquid gas into vapor gas, wherein said vaporizer comprises a single path vaporizer; an accumulator connected to said vaporizer to receive the vapor gas; a heated regulator to receive the vapor gas and control and control the pressure of the vapor gas; and a vapor bypass control loop downstream from the accumulator and prior to the heated regulator, wherein the single path vaporizer comprises an inner heated cartridge, a first metal layer surrounding the inner heater cartridge to promote uniform heating and eliminate hot spots, a second non-reactive metal layer surrounding the inner heater cartridge and a mesh layer.

2. A system for vaporizing and measuring liquid gas, comprising:
   a transmission device to transmit liquid gas;
   a vaporizer to receive a first amount of liquid gas and convert the first amount of liquid gas into vapor gas;
   an accumulator connected to said vaporizer to receive the vapor gas;
   a heated regulator to receive the vapor gas and control and control the pressure of the vapor gas;
   a vapor bypass control loop downstream from the accumulator and prior to the heated regulator;
   one or more test containers to store selectively receive and store respective samples of heated vapor gas output from the vaporizer; and
   an analysis device operable to receive vapor gas from said heated regulator and determine the constituent components of the vapor gas.

3. A system as claimed in claim 1, further comprising a thermal mass flow meter in the vapor bypass control loop.

4. A system as claimed in claim 1, further comprising a rotometer in the vapor bypass control loop.

5. A system as claimed in claim 1, further comprising insulation on tubing from a sample point to said vaporizer.

6. A system as claimed in claim 1, further comprising vacuum jacketing on tubing from a sample point to said vaporizer.

7. A system as claimed in claim 1, further comprising a microprocessor-based auto-tuner on a heater control board.

8. A system as claimed in claim 1, further comprising a temperature sensor for input of liquid to said vaporizer.

9. A system as claimed in claim 1, further comprising a cryogenic shut off valve to shut off the process liquid.

10. A system for vaporizing and measuring liquid gas, comprising:
- a transmission device to transmit liquid gas;
- a vaporizer to receive a first amount of liquid gas and convert the first amount of liquid gas into vapor gas;
- an accumulator connected to said vaporizer to receive the vapor gas;
- a heated regulator to receive the vapor gas and control and control the pressure of the vapor gas;
- a vapor bypass control loop downstream from the accumulator and prior to the heated regulator;
- wherein the accumulator comprises:
  - an impingement tube having a series of holes spaced at predetermined intervals to provide an increased stable vapor sample by promoting admixing within the accumulator tank; and
  - an extraction tube which protrudes into the accumulator tank to ensure heavy components which may partition to the inner wall of the accumulator are not being removed.

11. A method of measuring the constituent components of liquid gas, comprising: receiving the liquid gas into a vaporizing device; selectively directing the received liquid gas into a vaporizer within the vaporizing device, wherein said vaporizer comprises a singe path vaporizer; converting the liquid gas directed to the vaporizer into vapor gas; accumulating the vapor gas in a storage device; outputting the vapor gas accumulated in the storage device; directing a portion of outputted vapor gas from the storage device to a measuring device operable to determine the constituent components of the vapor gas; and directing a portion of outputted vapor gas from the storage device to a vapor return, wherein the singe path vaporizer comprises an inner heated cartridge, a first metal layer surrounding the inner heater cartridge to promote uniform heating and eliminate hot spots, a second non-reactive metal layer surrounding the inner heater cartridge, and a mesh layer.

12. A method according to claim 11, comprising:
- receiving the liquid gas into a top inlet of the vaporizing device; and
- outputting the vapor gas from a bottom outlet of the vaporizing device.

13. A system as claimed in claim 1, wherein said vaporizer comprises an inlet disposed at the top of the vaporizer and an outlet disposed at the bottom of the vaporizer.

14. A system as claimed in claim 1, comprising two vaporizers.

15. A system as claimed in claim 2, wherein said vaporizer comprises a single path vaporizer.

16. A system as claimed in claim 15, wherein the single path vaporizer comprises an inner heated cartridge, a first metal layer surrounding the inner heater cartridge, a second non-reactive metal layer surrounding the inner heater cartridge, and a mesh layer.

17. A system as claimed in claim 2, wherein said vaporizer comprises a multi-path vaporizer having at least three coils.

18. A system as claimed in claim 2, further comprising a thermal mass flow meter in the vapor bypass control loop.

19. A system as claimed in claim 2, further comprising a rotometer in the vapor bypass control loop.

20. A system as claimed in claim 2, further comprising insulation on tubing from a sample point to said vaporizer.

21. A system as claimed in claim 2, further comprising vacuum jacketing on tubing from a sample point to said vaporizer.

22. A system as claimed in claim 2, further comprising a microprocessor-based auto-tuner on a heater control board.

23. A system as claimed in claim 2, further comprising a temperature sensor for input of liquid to said vaporizer.

24. A system as claimed in claim 2, further comprising a cryogenic shut off valve to shut off the process liquid.

25. A system as claimed in claim 2, wherein said vaporizer comprises an inlet disposed at the top of the vaporizer and an outlet disposed at the bottom of the vaporizer.

26. A system as claimed in claim 2, comprising two vaporizers.

27. A system as claimed in claim 10, wherein said vaporizer comprises a single path vaporizer.

28. A system as claimed in claim 27, wherein the single path vaporizer comprises an inner heated cartridge, a first metal layer surrounding the inner heater cartridge, a second non-reactive metal layer surrounding the inner heater cartridge, and a mesh layer.

29. A system as claimed in claim 10, wherein said vaporizer comprises a multi-path vaporizer having at least three coils.

30. A system as claimed in claim 10, further comprising a thermal mass flow meter in the vapor bypass control loop.

31. A system as claimed in claim 10, further comprising a rotometer in the vapor bypass control loop.

32. A system as claimed in claim 10, further comprising insulation on tubing from a sample point to said vaporizer.

33. A system as claimed in claim 10, further comprising vacuum jacketing on tubing from a sample point to said vaporizer.

34. A system as claimed in claim 10, further comprising a microprocessor-based auto-tuner on a heater control board.

35. A system as claimed in claim 10, further comprising a temperature sensor for input of liquid to said vaporizer.

36. A system as claimed in claim 10, further comprising a cryogenic shut off valve to shut off the process liquid.

37. A system as claimed in claim 10, wherein said vaporizer comprises an inlet disposed at the top of the vaporizer and an outlet disposed at the bottom of the vaporizer.

38. A system as claimed in claim 10, comprising two vaporizers.

* * * * *

UNITED STATES PATENT AND TRADEMARK OFFICE
CERTIFICATE OF CORRECTION

| | | |
|---|---|---|
| PATENT NO. | : 8,056,399 B2 | Page 1 of 1 |
| APPLICATION NO. | : 12/364208 | |
| DATED | : November 15, 2011 | |
| INVENTOR(S) | : Kenneth O. Thompson et al. | |

It is certified that error appears in the above-identified patent and that said Letters Patent is hereby corrected as shown below:

col. 12, line 32: "receive the vapor gas and control and control" should be --receive the vapor gas and control-- col. 12, lines 47-48: "receive the vapor gas and control and control" should be --receive the vapor gas and control-- col. 12, lines 51-52: "to store selectively receive and store" should be --to selectively receive and store-- col. 13, lines 12-13: "receive the vapor gas and control and control" should be --receive the vapor gas and control--

Signed and Sealed this
Third Day of January, 2012

David J. Kappos
*Director of the United States Patent and Trademark Office*